United States Patent [19]

Garabet

[11] Patent Number: 5,443,506
[45] Date of Patent: Aug. 22, 1995

[54] LENS WITH VARIABLE OPTICAL PROPERTIES

[76] Inventor: Antoine L. Garabet, 840 N. Pennsylvania, Glendora, Calif. 91740

[21] Appl. No.: 977,663

[22] Filed: Nov. 18, 1992

[51] Int. Cl.$^6$ .................................................. A61F 2/16
[52] U.S. Cl. ........................................ 623/6; 351/161; 359/666; 359/667
[58] Field of Search ............................. 623/6; 351/161; 359/666, 667

[56] References Cited

U.S. PATENT DOCUMENTS

| | | | |
|---|---|---|---|
| 3,515,457 | 6/1970 | Dillon, Jr. | |
| 3,609,584 | 9/1971 | Stitch | |
| 4,037,929 | 7/1977 | Bricot et al. | |
| 4,190,330 | 2/1980 | Berreman | |
| 4,300,818 | 11/1981 | Schachar | |
| 4,313,651 | 2/1982 | Miller, Jr. | |
| 4,373,218 | 2/1983 | Schachar | 623/6 |
| 4,512,040 | 4/1985 | McClure | 623/6 |
| 4,601,545 | 7/1986 | Kern | 623/4 X |
| 4,720,286 | 1/1988 | Bailey et al. | 623/6 |
| 4,787,903 | 11/1988 | Grendahl | 623/6 |
| 4,816,031 | 3/1989 | Pfoff | 623/6 |
| 4,994,082 | 2/1991 | Richards et al. | 623/6 |
| 5,066,301 | 11/1991 | Wiley | 623/6 |
| 5,275,623 | 1/1994 | Sarfarazi | 623/6 |

Primary Examiner—Mary Beth O. Jones
Attorney, Agent, or Firm—Knobbe, Martens, Olson & Bear

[57] ABSTRACT

A variable focus intraocular lens system alters the type of medium which is located between two lens surfaces of the intraocular lens system to alter the accommodation of the lens. A continuous flow path is created in the intraocular lens system which controls the flow of fluid into the optical zone of the intraocular lens. The continuous flow path contains multiple discrete segments of fluid which move through the fluid path of the lens system. The fluid segments can include segments of positively charged fluids, negatively charged fluids, air, oil, water or other fluids. The electric potential that is generated when the ciliary body contracts and relaxes is used to attract and repel certain charged fluid segments to control the type of media that is contained in the optical zone of the lens. By varying the type of media contained in the optical zone, the accommodation of the intraocular lens system can be altered. Further, by utilizing the charge generated by the contraction and relaxation of the ciliary body to move the fluid segments, no external power sources or signals are required to change the accommodation of the variable lens system of the present invention.

17 Claims, 7 Drawing Sheets

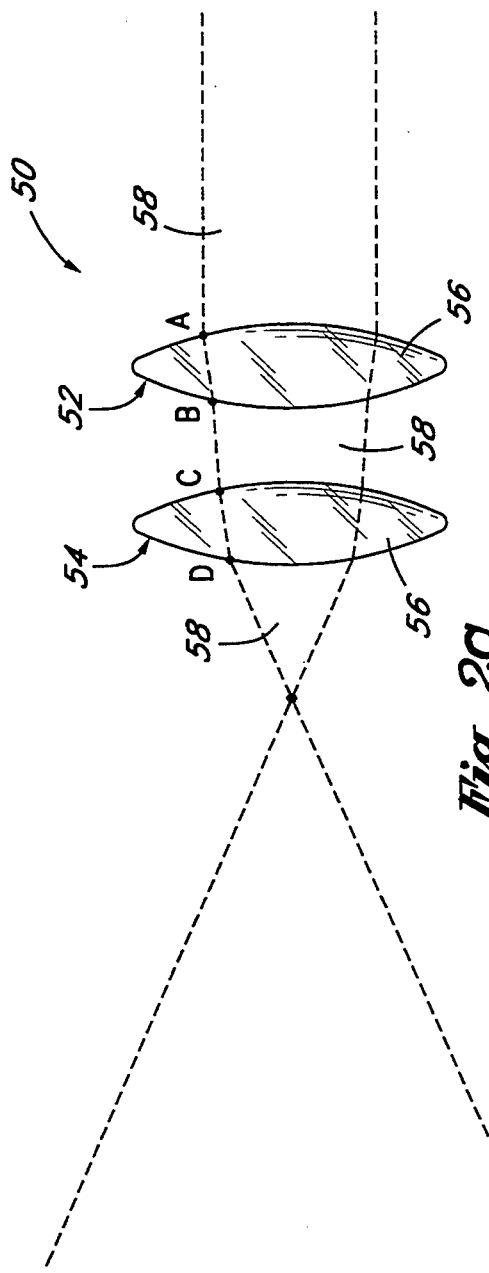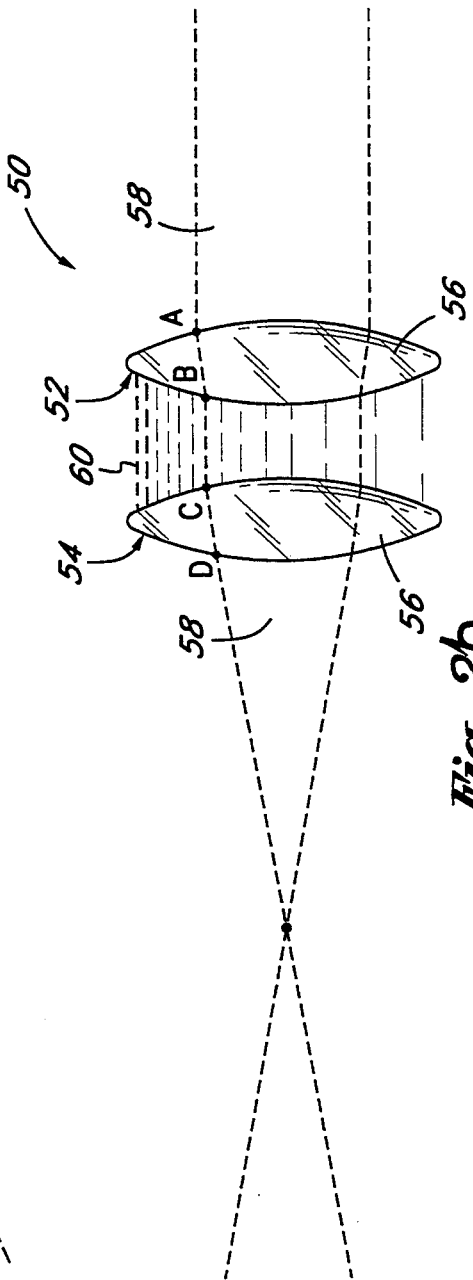

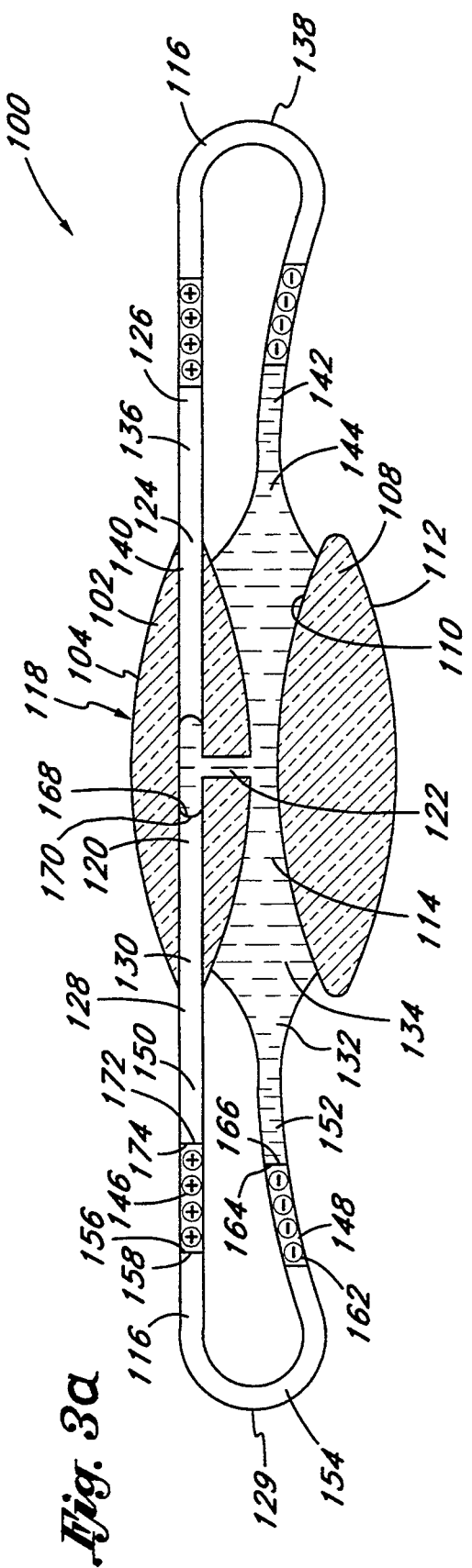
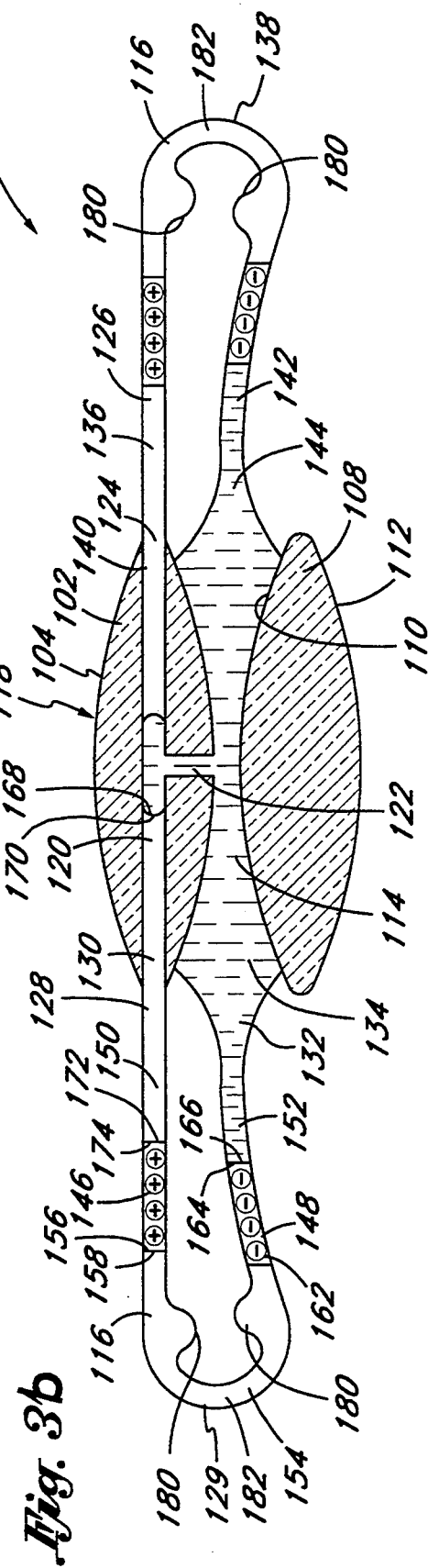

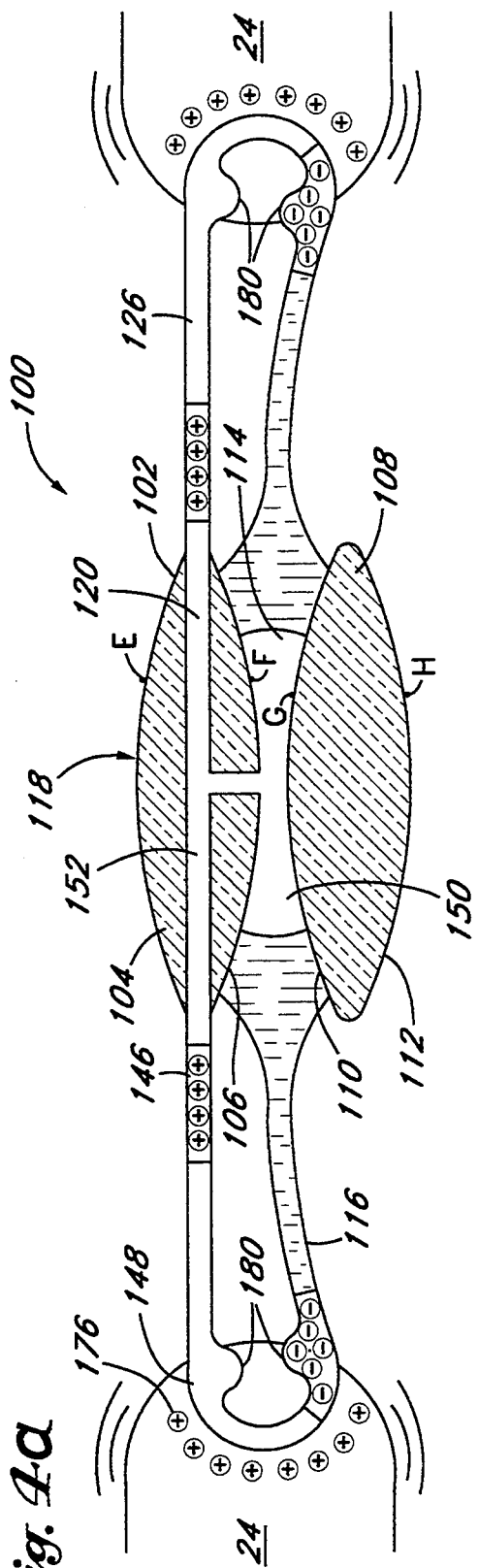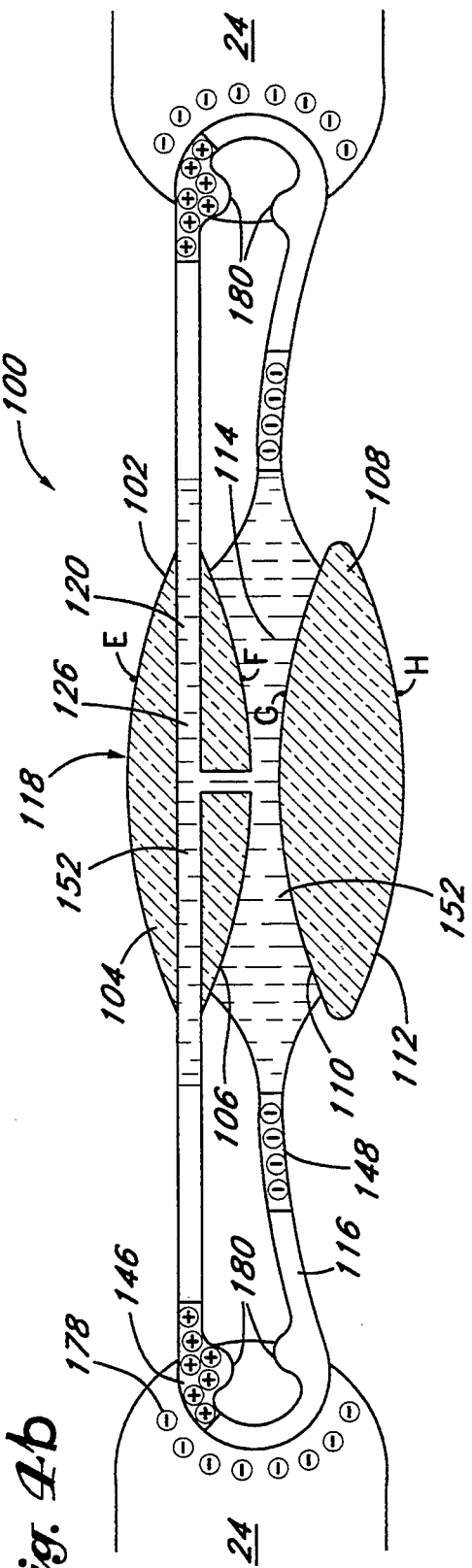

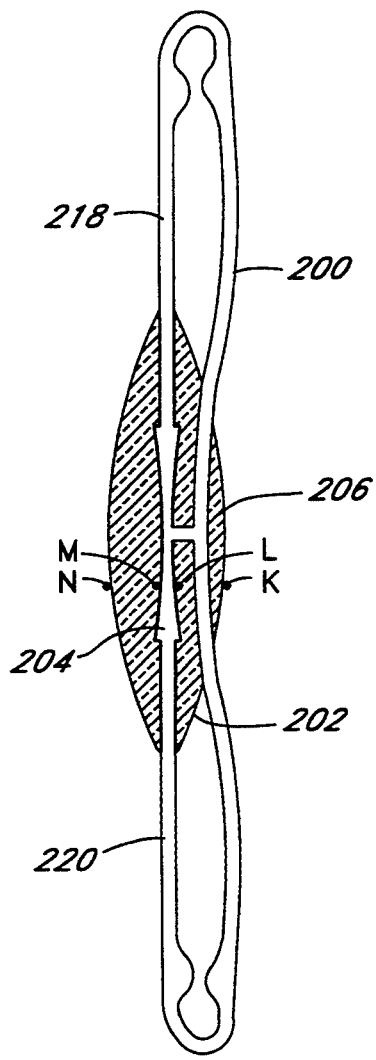
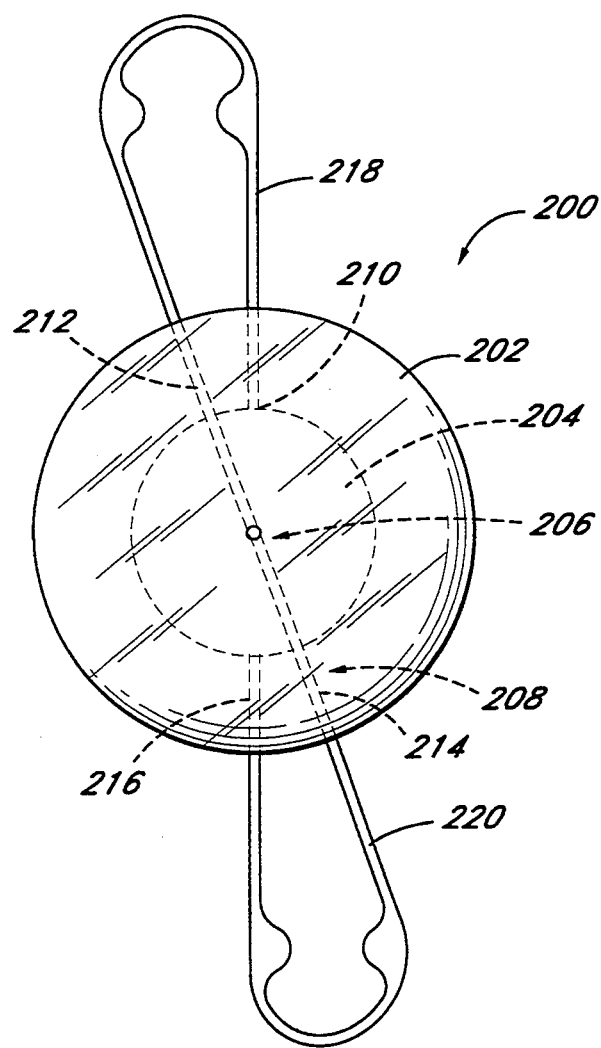

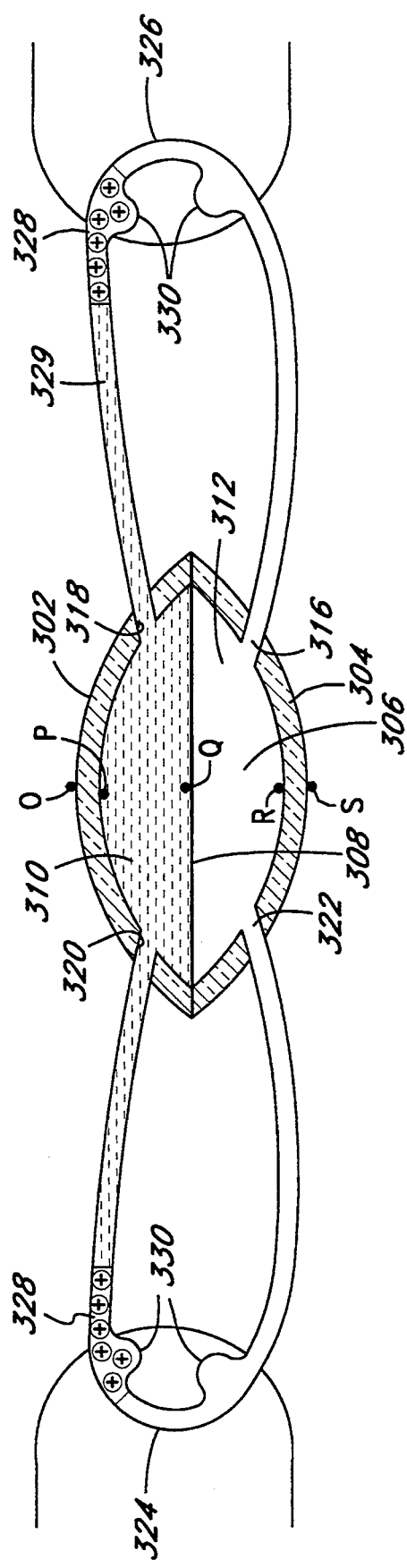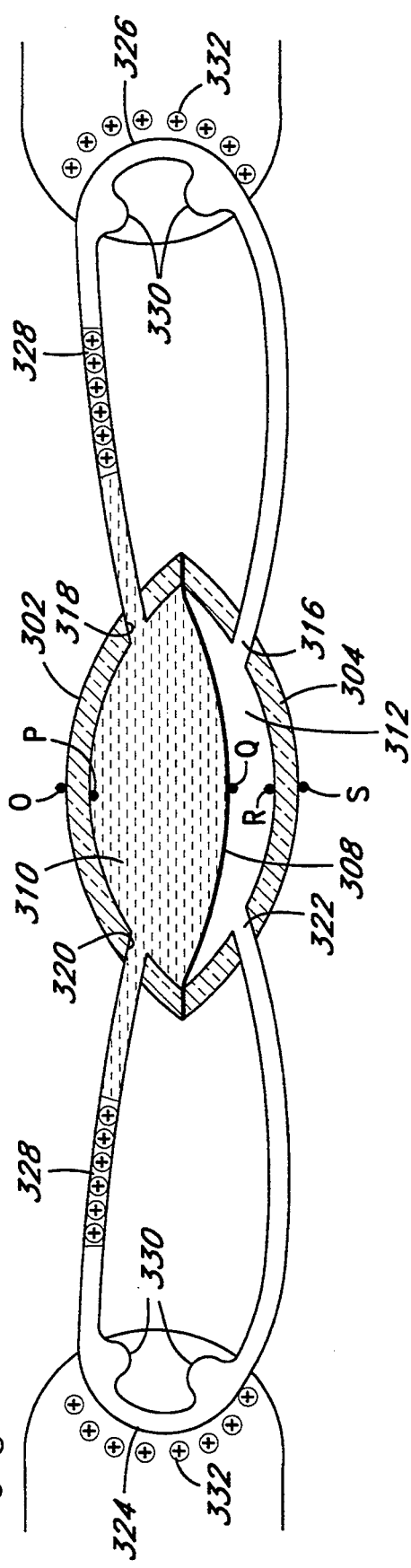

LENS WITH VARIABLE OPTICAL PROPERTIES

BACKGROUND OF THE INVENTION

The present invention relates to intraocular lenses, and, more particularly, to intraocular lenses having variable optical properties.

The crystalline lens of the eye is susceptible to, among other impairments, the growth of cataracts. In this condition, the light that would normally pass through the lens to the retina is blocked by the clouded lens.

Various ailments including cataractous tissue growth in the lens can necessitate or desirably be treated by the removal of the crystalline lens of the eye. The natural lens thereafter is replaced with an artificial lens referred to as an intraocular lens ("IOL"). Although the development of IOL's provided significant relief for some patients, the known IOL's only imperfectly mimic the functioning of the natural lens. For example, artificial lenses are generally not elastic like the crystalline lens of the eye and cannot alter their focusing power like the normal crystalline lens of the eye. As a result, the known IOL's generally do not permit continuous adjustment of the focal power of the lens.

Some attempts have been made to provide an intraocular lens that has a variable accommodation. One approach is to provide an IOL with multiple lens surface each with a different radius of curvature. These multi-focal lenses utilizes the same principles as multi-focal eye glasses which enable the user to look through different portions of the lens to achieve different levels of diopter power. However, the levels of diopter power are fixed with the different radii of curvature of the lens surfaces and do not provide for variable levels of focusing power.

Another common approach to varying the focus of an IOL is to form a conventional hard intraocular lens with a flexible outer surface made from a material such as silicone. Water is then injected in between the conventional hard portion of the lens and the flexible outer surface of the lens. The water will stretch the outer flexible layer to change the radius of curvature of the intraocular lens and thereby change the accommodation of the lens. One disadvantage of this approach is that a fluid source, a fluid pump and a flow control valve all must be provided within close proximity to the lens. As the area around the crystalline lens of the eye is quite confined, most of the fluid injection components have to be provided on the lens itself. Further, an energy source must be provided to pump the fluid. As there is no mechanical force generated in the eye that is strong enough to pump the fluid, an external power supply is required to run the pump. Such an external power supply is usually implemented using a battery which has a limited life cycle.

A further approach that has been used to vary the accommodation of an IOL is the coating of a conventional IOL with a liquid crystal material. A voltage source is applied to the crystal material to polarize the crystals. Once the crystals are polarized the refractive index of the crystalline material changes thereby changing the accommodation of the IOL. One principal disadvantage of this type of system is the relatively large amount of energy that is required to polarize the liquid crystal material, on the order of 25 volts. As there is no known manner of generating that level of voltage within the body, an external power source, such as a battery, is therefore necessary.

The above described and other prior attempts to provide an intraocular lens with variable accommodation are generally complex systems. These complex systems are costly to manufacture and often times impractical to implement in the eye of a human. In addition, the above systems require external power sources, such as batteries, which have a limited life cycle and may require surgery to replace. Therefore, a need exists for a simple IOL with variable accommodation that only relies on the forces provided by the human body for operation.

SUMMARY OF THE INVENTION

In accordance with one aspect of the present invention, there is provided a variable focus intraocular lens which comprises an intraocular lens which varies the presence of a medium between two lens surfaces of the intraocular lens system to alter the accommodation of the lens system.

A preferred embodiment of the intraocular lens system of the present invention comprises a first optical component with at least a first lens surface, a second optical component with at least a second lens surface, a fluid reservoir between the first and second lens surfaces, and at least one continuous flow loop. The continuous flow loops connect the fluid reservoir between the two lens surfaces to a channel in a first portion of the intraocular lens. Preferably, the continuous flow loop comprise a piece of narrow tubing which contains the fluid in the flow path. In addition, the continuous flow loops are used to position and hold, the intraocular lens system in the eye. The continuous flow loops, the fluid channel and the fluid reservoir together define a continuous fluid flow path in the intraocular lens system.

The fluid path of the preferred embodiment contains multiple discrete segments of fluid which move through the fluid path of the lens system. The fluid segments include a segment of a positively charged fluid, negatively charged fluid, air, and at least one segment of oil, water or another fluid. There are no physical dividers in the narrow tubing to separate these fluid segments. The fluids themselves must be carefully chosen to ensure that a meniscus of sufficient strength will be formed at the fluid junction to keep two abutting segments of fluid separate and distinct. Additional segments of fluid may be added as long as positively charged fluids do not abut negatively charged fluids at any fluid juncture.

The ciliary body is the portion of the eye that is in charge of accommodation. When the ciliary body fires, an electrical action potential is created. When the ciliary body relaxes a potential of reverse charge is released. The continuous flow loops of the intraocular lens of the present invention are formed in the shape of conventional haptics and are anchored in the ciliary sulcus, a grove located between the ciliary body and the iris. When positive and negative charges are generated in the ciliary body they impact the charged fluid within the continuous flow loops. When a positive charge is generated in the ciliary body, the negatively charged fluid segment is attracted towards the ciliary body, and the positively charged fluid segment is repelled from the ciliary body, and visa versa. The applied charge thereby controls the position of the fluid segments within the continuous flow path. Preferably, the fluid segments are positioned such that when the ciliary body contracts, the segment of appropriately charged fluid will be attracted towards the ciliary body, and the segment containing air will be forced into the optical zone of the lens system increasing its diopter power. Further, when the ciliary body relaxes, the segment of appropriately charged fluid will be attracted toward the ciliary body, and the segment containing oil, water or another fluid is forced into the optical zone of the lens system decreasing its diopter power. When the fluid segment that contains air is located in the optical zone, i.e., in the reservoir between the two lens surfaces and in the fluid channel, the total focusing power of the lens system is high. When the segment containing water, oil or another fluid with a refractive index which is close to that of the lens material is located in the optical zone, i.e., in the fluid reservoir between the two lens surfaces and in the fluid channel, the total focusing power of the system is lower. Thus by providing variable fluid segments between the two lens surfaces, the lens system of the present invention is able to provide variable focusing power. Further, by utilizing the electric field generated by the action potential of the ciliary body to move the fluid segments within the fluid path, no external power sources are required to operate the lens system of the present invention.

BRIEF DESCRIPTION OF THE DRAWINGS

FIG. 2a is a cross sectional view of a dual lens system with air separating the two lenses.

FIG. 2b is a cross sectional view of a dual lens system with water separating the two lenses.

FIG. 3a is a cross sectional view of a preferred embodiment of a dual loop intraocular lens system of the present invention.

FIG. 3b is a cross sectional view of a preferred embodiment of a dual loop intraocular lens system of the present invention where each flow loop includes two fluid receptacles.

FIG. 4a is a cross sectional view of a preferred embodiment of the dual intraocular lens system of the present invention installed in a human eye illustrating the eye attempting to focus on a close object utilizing the dual intraocular lens system of the present invention.

FIG. 4b is a cross sectional view of a preferred embodiment of the dual intraocular lens system of the present invention installed in a human eye illustrating the eye attempting to focus on a far object utilizing the dual intraocular lens system of the present invention.

FIG. 5a is a cross sectional view of an alternate embodiment of the intraocular lens system of the present invention which utilizes a single lens.

FIG. 5b is a top plan view of an alternate embodiment of the intraocular lens system of the present invention.

FIG. 7a is a cross sectional view of another alternative embodiment of the intraocular lens system illustrating the eye focussing on a far object.

FIG. 7b is a cross sectional view of another alternative embodiment of the intraocular lens system illustrating the eye attempting to focussing on a close object.

DETAILED DESCRIPTION OF THE INVENTION

Figure 1:
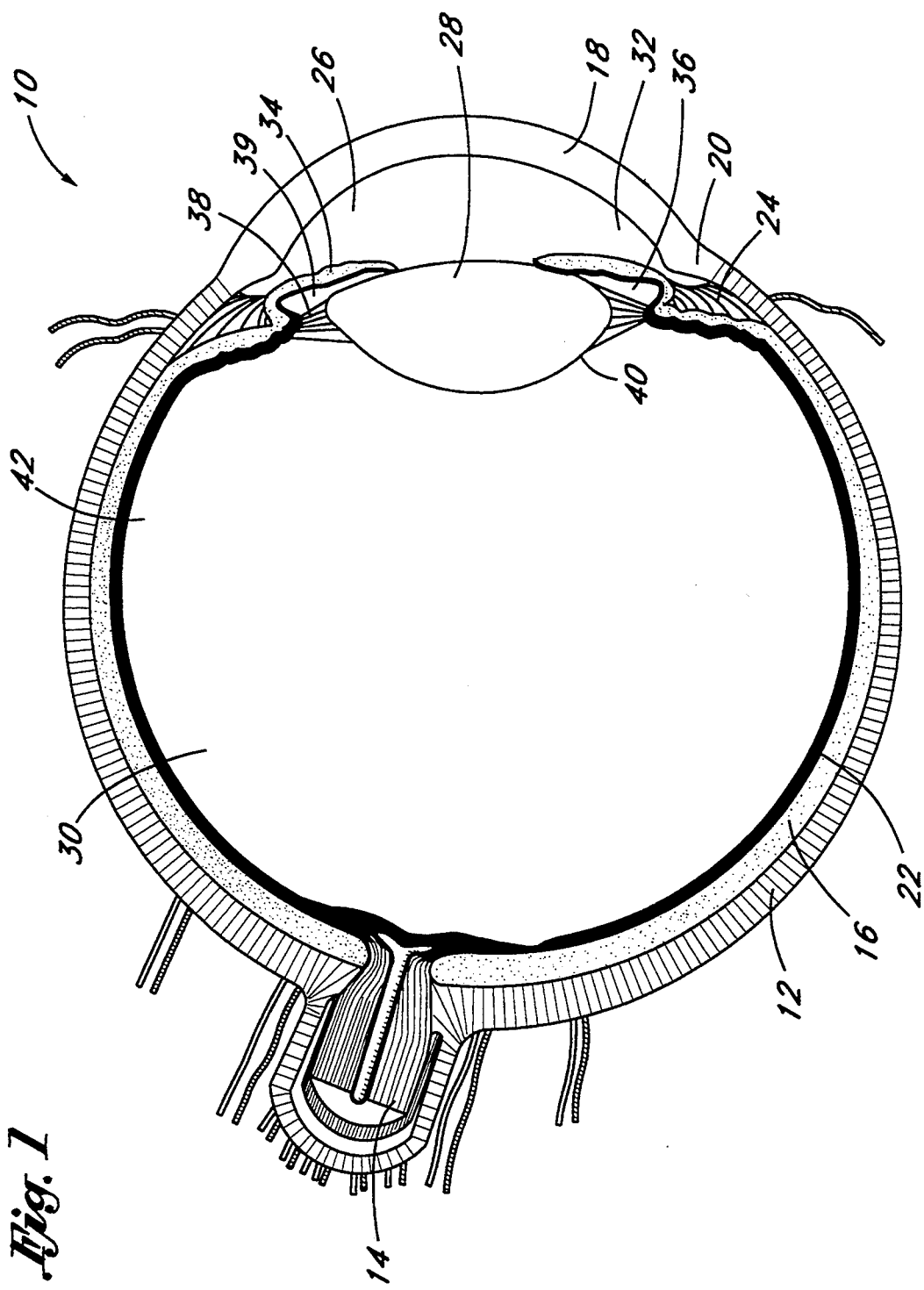
FIG. 1 is a cross sectional view of a human eye.

Referring to FIG. 1, the outer surface of an eye 10 is composed of connective tissue referred to as a sclera 12 which covers about 5/6 of the surface of the eye 10. At its thickest posterior part, the sclera 12 measures approximately 1 mm thick. The sclera 12 is tightly attached posteriorly to an optic nerve 14 of the eye 10, and to the choroid 16. Anteriorly the sclera 12 is continuous with the transparent cornea 18 which will be described in more detail later. The point of junction of the sclera 12 to the cornea 18 is referred to as the limbus 20. The next tissue layer of the eye 10 is the choroid 16 which is loosely attached to the sclera 12 along substantially their entire contact area. The choroid 16 is a thin highly vascular membrane which provides nutrients to the retina 22. The blood vessels of the choroid 16 are fed by the posterior ciliary arteries.

Six to seven millimeters behind the limbus 20 the choroid 16 is thickened and tightly attached to the sclera 12 and forms the ciliary body 24. The ciliary body 24 consists of unstripped fibers and forms a grayish, semitransparent circular band of about 3 millimeters broad on the outer surface of the anterior part of the choroid 16. Most of the bulk of the ciliary body 24 is formed by the vascular layer of the choroid 16 but this body also contains smooth muscle fibers that form the ciliary body 24. Most of the muscle fibers of the ciliary body 24 are longitudinal or radial extending fibers.

The next innermost layer is the retina 22. The retina 22 is a delicate nervous membrane upon which the images of the external objects are reflected. The posterior surface of the retina 22 is in contact with the choroid 16, its inner or anterior surface is in contact with the vitreous body 30. Light images are reflected upon the retina 22, and delivered to the brain through the optic nerve 14.

In order for light to reach the retina 22, it is directed through the refracting media of the eye 10 which comprises a cornea 18, aqueous humor 26, crystalline lens 28, and the vitreous body 30. First, the light enters through the cornea 18 which is transparent, convex anteriorly and projects like a dome beyond the sclera 12 of the eye 10. The cornea 18 has a tendency to bend or reflect light rays that pass through them but the cornea 18 consists mostly of connective tissue. Next the light passes through the anterior chamber 32 of the eye 10 which lies between the cornea 18 and the iris 34. The anterior chamber 32 is filled with a fluid, aqueous humor 26, which is constantly being produced and drained off through spaces that permeate through the tissues of the eye 10 such as through the sinus venosus sclera or canal of Schlemm.

Light then passes through the aperture formed at the center of the iris 34 to the posterior chamber 36 of the eye 10. The iris 34 of the eye 10 is a circular contractible disk suspended in the aqueous humor 26 of the eye 10 between the cornea 18 and the lens 28. The iris 34 is continuous with the ciliary body 24 and is connected to the cornea 18. A small grove called the ciliary sulcus 39 is formed between the iris 34 and the main portion of the ciliary body 24 where the two are joined together. The iris 34 divides the space between the lens 28 and the cornea 18 into the anterior 32 and posterior 36 chambers. The most important feature of the iris 34 is its ability to change the diameter of the pupil in a fashion somewhat similar to the change in aperture of a camera diaphragm. This change is brought about by smooth muscle lying in the iris 34. When the muscle contracts, it reduces the size of the pupil, thus protecting the retina 22 from excessive or unneeded light. When more light is needed, the iris 34 expands thus allowing more light to be provided to the retina 22. The light that passes through the aperture of the iris 34 then passes through the posterior chamber 36 of the eye 10 which lies between the iris 34 and the zonular fibers 38. The posterior chamber 36 is also filled with aqueous humor 26 and enables the light to pass directly to the crystalline lens 28 of the eye 10.

The crystalline lens 28 of the eye 10 lies immediately behind the iris 34 and is encased in the lens capsule 40. The lens 28 of the eye 10 is a biconvex disk measuring about 9 to 10 millimeters in diameter and about 4 to 5 millimeters in anteroposterior thickness. Its posterior surface is more highly curved than its anterior one. The lens 28 is formed of an elastic material but is held under tension in the lens capsule 40 by the zonular fibers 38 in a somewhat flattened shape. The lens capsule 40 is a transparent structureless membrane which is thicker in front then behind. The lens 28 is held in place in the eye 10 by the zonular fibers 38 which are attached to the lens capsule 40 at one end and the ciliary body 24 at the other. The lens 28 is the only refracting medium of the eye 10 whose reflecting ability can be varied from moment to moment to maintain visual acuity which will be described in more detail below.

After passing through the lens 28, the light is delivered to the large vitreous chamber 42 in the posterior aspect of the eye 10. The vitreous chamber 42 is filled with a gelatinous transparent mass known as the vitreous body 30 frequently referred to as the vitreous humor. In contrast to the aqueous humor 26, the vitreous body 30 does not undergo constant replacement. It is formed early in the development of the eye 10 and cannot be replaced thereafter. From the vitreous body 30, the light is delivered to the retina 22, and ultimately to the optic nerve 14.

The ciliary body 24 as described above is the chief agent in accommodation, i.e., in adjusting the eye 10 to vision of near objects. In the resting normal eye 10, the ciliary body 24 is relaxed and the refraction brought about by the flattened lens 28 of the eye 10 is just enough to bring an object seen at a distance, from which the light rays are traveling approximately parallel once they reach the eye 10, into sharp focus onto the retina 22 of the eye 10. The closer an object is to the eye 10, the more the light rays from that object diverge as they approach the eye 10, and therefore the more refraction there must be in order to bring these light rays into focus on the retina 22.

In order to bring about this greater change of refraction, the shape of the crystalline lens 28 of the eye 10 must become more convex. The ciliary body 24 is the main muscle used to change the shape of the crystalline lens 28 of the eye 10. When the ciliary body 24 contracts, it relaxes the suspensory ligaments of the crystalline lens 28, the zonular fibers 38, and thus allows the lens 28 to become more convex. The muscles of the ciliary body 24 all presumably function to narrow the diameter of the ring formed by the ciliary body 24 thus releasing tension on the zonular fibers 38 which allows the lens 28 to expand. Although the expansion of the lens 28 appears to be a passive process, brought about by the elasticity of the lens material itself, it should be noted that near vision requires the presence of a muscular force which is provided by the ciliary body 24. The variation in the tension on the zonular fibers 38 by the ciliary body 24 effects the accommodation of the lens 28 and thereby changes the focal point of the lens 28.

The crystalline lens 28 of the eye 10 has the same optical properties as a conventional lens, except that the crystalline lens 28 has the ability to change its shape and thereby change the linear magnification provided by the crystalline lens 28. In the resting eye 10 the crystalline lens 28 is most flattened, the resting eye 10 is adapted to distance vision and not close vision, a muscular contraction is required to change the shape of the crystalline lens 28 to enable close vision.

A typical prosthetic IOL which is used to replace the crystalline lens 28 of the eye 10 can not change its shape. As a consequence, the optical properties of the intraocular lens are static, the diopter power of the IOL cannot be changed to accommodate the vision of near objects. The diopter power of each surface of a conventional intraocular lens is defined by the equation below:

$$P = (n_2 - n_1)/r_c \tag{1}$$

Where P is the Power of the lens surface in diopters, $n_1$ is the refractive index of the first medium, $n_2$ is the refractive index of the second medium and $r_c$ is the radius of curvature, in meters, of the lens surface that the light is refracted through.

The total power of a lens is the algebraic sum of the power of its surfaces. In order to alter the power of the lens, either the radius of curvature of the lens surfaces must be changed, or the refractive index of one of the two mediums must change. The crystalline lens 28 of the eye 10 changes its magnification by changing the radius of curvature of the lens.

In a typical dual lens system 50 with a first 52 and second 54 lens having two different lens surfaces as schematically illustrated in FIG. 2a, light is refracted at four surfaces labeled as A, B, C, and D. For the purposes of the example, the first and second lenses 52, 54 are assumed to be made of polymethylmethacrylate (PMMA) 56, a typical IOL lens material, which has a refractive index of 1.49. The medium in between the two lenses 52, 54 and surrounding the two lenses 52, 54 is assumed to be air 58 which has a refractive index of 1.0, the radius of curvature of surfaces A and C are assumed to be +0.01 m, and the radius of curvature of surfaces B and D are assumed to be −0.01 m. At surface A, the light is propagated from a first media, air 58, and a second media, PMMA 56. Thus $n_1 = 1.0$, $n_2 = 1.49$, and $r_c = +0.01$ m. Solving equation 1 above, the power at surface A is 49 diopters (D). At surface B, the light is refracted by propagating across a surface from a first media, PMMA 56, to a second media, air 58, thus $n_1 = 1.49$, $n_2 = 1.0$, and $r_c = -0.01$ m. Solving equation 1 above, the power at surface B is 49 D. Surface C yields a similar result as surface A, and surface D yields a similar result as surface B. The overall power for the entire system is the algebraic sum of the power (P) at each lens surface A, B, C and D. Thus the total system power is $P_A + P_B + P_C + P_D$ or $49 + 49 + 49 + 49$ which results in a total power for the lens system of 196 D.

FIG. 2b illustrates the dual lens system 50 illustrated in FIG. 2a, with a liquid medium such as water 60 suspended in between the two lenses. Light is still refracted at each of the four surfaces A, B, C, and D, but the refraction at surfaces B and C is significantly reduced. For the purposes of the example illustrated in FIG. 2b, the lenses are also assumed to be made of polymethylmethacrylate (PMMA) 56 which has a refractive index of 1.49, the medium in between the two lenses is assumed to be water 60 which has a refractive index of 1.33, the medium outside of the first and second lenses 52, 54 is assumed to be air 58 with a refractive index of 0, the radius of curvature of surfaces A and C are assumed to be +10 mm, and the radius of curvature of surfaces B and D are assumed to be −10 mm. At surface A, the light is refracted at the interface of the two media the first is air 58 and the second is PMMA 56, thus $n_1 = 1.0$, $n_2 = 1.49$, and $r_c = +0.01$ m. Solving equation 1 above, the power at surface A is 49 D. At surface B, the light is propagated from a first media, PMMA 56, to a second media, water 60, thus $n_1 = 1.49$, $n_2 = 1.33$, and $r_c = -0.01$ m. Solving equation 1 above, the power at surface B is 16 D. Surface C yields a similar result as surface B, and surface D yields a similar result as surface A. The overall power for the entire lens system is the algebraic sum of the power (P) at each lens surface A, B, C and D. Thus the total system power is $P_A + P_B + P_C + P_D$ or $49 + 16 + 49 + 16$ which results in a total system power of 130 D.

Comparing the results of the power of the dual lens system of FIG. 2a with air 58 suspended between the two lenses 52, 54 to the system of FIG. 2b with water 60 suspended between the two lenses 52, 54, the overall diopter power of the dual lens system is reduced by 66 D from 196 D to 130 D by simply suspending water between the two lenses. The total diopter change of the lens system will be reduced when the lens system is placed in the eye 10, because the lens system will be surrounded by aqueous humor 26 instead of air 58. The refractive index (n) of aqueous humor 26 is closer to the refractive index of water 60 then is the refractive index of air 58. Therefore the change in diopter power of a lens system within the aqueous humor 26 of an eye 10 by the introduction of water 60 or other optically active fluid will be significantly less than the change in diopter power of the same system in air 58.

The present invention incorporates the effect illustrated in the above exemplary lens system 50 into an intraocular lens system, thus enabling the intraocular lens to vary its focus. Although the preferred embodiments of the present invention are adapted for use as IOL's, the present invention can be readily adapted for use in any of a wide variety of other applications as will be apparent to one of skill in the art.

A preferred embodiment 100 of the present invention, as illustrated in FIG. 3a, is an intraocular lens system which varies the presence of a medium between two surfaces to alter the accommodation of the system. In general, the dual intraocular lens system of a preferred embodiment 100 comprises a first lens 102 with anterior 104 and posterior 106 lens surfaces, a second lens 108 with anterior 110 and posterior 112 lens surfaces, a fluid reservoir 114 between the first and second lenses 102, 108 and at least one continuous flow loop 116. Preferably as illustrated in FIG. 3, two flow loops 116 are used. An optical zone 118 is defined in the center of the lens system and is sized to conform with the optical zone of the crystalline lens 28 of the eye 10.

In a preferred embodiment of the lens system 100, the first lens 102 and the second lens 108 are preferably made from PMMA, however any of a variety of other biocompatible lens materials, such as silicone, can be used. The shape, i.e., radius of curvature, of the anterior surface 104 of the first lens 102 and the posterior surface 112 of the second lens 108 is determined by the power of the patients natural lens, which is determined by the curvature of the cornea and the length of the eye taken along the optical axis of the eye. The radius of curvature of the posterior lens surfaces 106 of the first lens 102 and the anterior lens surface 110 of the second lenses 108 are determined by the level of change in the power of the lens system that is desired. The more change that is desired the larger the radius of curvature of the posterior lens surfaces 106 of the first lens 102 and the anterior lens surface 110 of the second lenses 108.

The first and second lenses 102, 108 are preferably between 4 mm and 6.5 mm in diameter and between 0.5 mm and 2 mm in thickness to enable the lenses to fit within the space between the anterior 32 and posterior chamber 36 of the eye 10. The first and second lenses 102, 108 can be formed using conventional IOL molding techniques, however any other known lens forming techniques known to one skilled in the art can be used.

In the illustrated embodiment, the first lens 102 has a fluid channel 120 which extends longitudinally through the entire diameter of the first lens 102. A branch path 122 extends at a perpendicular to the fluid channel 120 starting at the center of the optical zone 118. The fluid channel 120 and the branch path 122 can be formed by mechanical drilling, laser drilling, or by any other boring means which will be appreciated by one skilled in the art.

The continuous flow loops 116 connect the fluid reservoir 114 between the two lenses 102, 108 to the lateral ends of the fluid channel 120 in the first lens 102. More than two flow loops 116 can be used to define additional fluid paths in the intraocular lens system, i.e., three or four or more flow loops 116 can be used. However, each additional flow loop 116 adds a level of complexity and weight to the system which may not be required depending upon the application, therefore the preferred embodiment of the present invention is provided with two flow loops 116.

The continuous flow loops 116 are contained in a media for providing a flow path 126, such as one or more pieces of transparent narrow tubing. Preferably, lightweight, tubing made from a biocompatible material, such as PMMA, is used. The tubing extends from the fluid channel 120 in the first lens 102 towards the ciliary body 24 for attachment and back to the fluid reservoir 114 to complete the formation of the continuous fluid flow loop 116.

A first end 128 of a first continuous flow loop 129 is connected to a first side 130 of the fluid channel 120 and a second end 132 of the first continuous flow loop 129 is connected to a first side 134 of the fluid reservoir 114. A preferred embodiment of the intraocular lens system of the present invention 100 is symmetrical about the optical axis, so the components which are discussed on the first side of the system preferably have identical counterparts on a second side of the lens system. Therefore, a first end 136 of a second continuous flow loop 138 is connected to a second side 140 of the fluid channel 120 and a second end 142 of the second continuous flow loop 138 is connected to a second side 144 of the fluid reservoir 114.

Preferably, the narrow pieces of transparent tubing of the continuous flow loops 116 are connected to the fluid channel 120 in the IOL and to the fluid reservoir 114 by the following described procedure. Preferably, the tubing is chosen such that the end of the tubing has a slightly reduced outer diameter than the remainder of the tubing length. The reduced diameter tubing is sized to enable insertion of the first tubing end into an end of the fluid channel 120 to ensure that a self contained fluid path 126 results. The second end of the reduced diameter tubing is inserted into an end of the fluid reservoir 114. The tubing is attached to the fluid channel 120 and the fluid reservoir 114 by any number of common bonding techniques, such as thermal bonding, adhesive bonding, or any other bonding methods available to those skilled in the art.

The flow loops 116 function to contain a continuous flow path 126 of communication within the intraocular lens system. The continuous flow path begins in the fluid channel 120 at the optical zone 118 of the lens systems and extends down through the branch flow path 122 into the fluid reservoir 114 between the first and second lenses 102, 108. The flow path 126 extends outward from the fluid reservoir 114 through the flow loops 116 back to the fluid channel 120 in the first lens 102 and into the optical zone 118.

The continuous flow path 126 of a preferred embodiment of the lens system 100 contains multiple discrete segments of fluid which move through the intraocular lens system. Preferably, the fluid segments include a segment of a positively charged fluid, a negatively charged fluid, an air bubble, and at least one segment of optically active fluid, such as oil, water or other fluid. The segment of positively charged fluid is separated from the segment of negatively charge fluid by a segment of oil, water or other fluid. Preferably the segment of positively charged solution is a sodium ion solution, however any biocompatible positively charged solution can be used. Further, the segment of negatively charged solution is preferably a chlorine ion solution, however any biocompatible negatively charged solution can be used.

Preferably, there are no physical dividers in the flow loops 116 or elsewhere in the fluid path 126 to separate the fluid segments. The fluids themselves must be carefully chosen to ensure that a meniscus of sufficient strength will be formed between each set of abutting segments of fluid to keep them separate and distinct. Additional segments of fluid may be added as long as positively charged fluids do not abut negatively charged fluids at any fluid juncture. The fluid segments are introduced into the tubing using suction or any other conventional fluid transfer techniques known to one skilled in the art.

In a preferred embodiment of the lens system 100 as illustrated in FIG. 3, the fluid segments comprise a segment of positively charged fluid 146, a segment of negatively charged fluid 148, a segment of air 150, a segment of water 152, and a segment of another non-charged optically active fluid 154. In the preferred embodiment, the segments are arranged such that a first side 156 of a segment of positively charged fluid 146 abuts a first side 158 of a segment of optically active fluid 154, such as air, water or other fluid. A second side 160 of the fluid segment containing an optically active fluid 154, such as air, water, or any other optically active fluid, abuts a first side 162 of the segment of negatively charged fluid 148. A second side 164 of the segment of negatively charged fluid 148 abuts a first side 166 of a segment of water 152. A second side 168 of the segment of water 152 abuts a first side 170 of a segment of air 150. A second side 172 of the segment of air 150 abuts a second side 174 of a positively charged fluid segment 146 which completes the continuous flow path 126.

The preferred embodiment of the intraocular lens system 100 of the present invention is inserted into the eye 10 using a procedure similar to a standard intraocular lens installation procedure. The continuous flow loops 116 are inserted in the ciliary sulcus 39, using the same procedure as the attachment of conventional IOL haptics. The continuous flow loops 116, not only are used to create the continuous flow path 126, but are also used to position and hold the intraocular lens system of the present invention in the eye 10. The continuous flow loops 116 are positioned such that the optical zone 118 of the lens system is aligned with the physiological optical zone of the patient's eye 10.

FIG. 3b illustrates a preferred embodiment of a dual loop intraocular lens system as shown in FIG. 3a where each of the continuous flow loops 116 includes the addition of two fluid receptacles 180. The fluid receptacles 180 are positioned in the continuous flow loops 116 to trap the segments of positively and negatively charged fluid 146, 148 as they approach the ciliary body 24 without enabling the fluid to reach a limiting bend 182 of the continuous flow loop 116. If either of the positively and negatively charged fluids 146, 148 reaches the limiting bend 182 of the continuous flow loop 116 and flows to the opposite side of the flow loop 116 the pattern of accommodation will be disturbed. Therefore, the addition of the fluid receptacles 180 on either side of the limiting bend 182 of the continuous flow loop 116 will keep the segments of positively and negatively charged fluids 146, 148 on their respective sides of the flow loop 116.

A preferred embodiment of the intraocular lens system of the present invention 100, as illustrated in FIG. 3b, functions as described below in connection with FIGS. 4a and 4b. When the eye 10 attempts to focus on a close object, the muscle of the ciliary body 24 contracts. The contraction of the ciliary body 24 generates a voltage of certain power and direction within and around the ciliary body 24, for the purpose of this discussion we will assume a positive charge results with the contraction of the ciliary body 24. As illustrated in FIG. 4a, when a potential charge 176 from the ciliary body 24 is positive, the segment of negatively charged fluid 146 is drawn towards the ciliary body 24 and the segment of positively charged fluid 146 is repelled away from the ciliary body 24. As the positively charged fluid segment 146 moves away from the ciliary body 24 and the negatively charge fluid segment 148 is drawn towards the ciliary body 24, the other fluid segments are forced to move through the continuous flow path 126. The negatively charged fluid segment 148 will begin to fill the fluid receptacle 180 as the pull of the positive potential draws the negative fluid towards the ciliary body 24 without allowing the positively charged fluid segment flow to the other side of the continuous flow loop 116. The fluid segments are positioned in the continuous flow loop 116 such that when the negatively charged fluid segment 148 is drawn toward the ciliary body 24, the segment of air 150 is forced into the optical zone 118 of the lens system. The segment of air 150 will fill at least the portion of the fluid reservoir 114 and the portion of the fluid channel 120 in the first lens 102 that are within the optical zone 118.

As described above in connection with FIG. 2a, the effective power of the lens system illustrated in FIG. 4a is the algebraic sum of the power of each lens surface.

When the segment of air 150 is used to separate the first and second lenses 102, 108 of the intraocular lens system, there are four surface junctions E, F, G and H. Using equation 1 above, the effective power at each lens surface junction E, F, G and H can be calculated given the radius of curvature, in meters, of each lens surface 104, 106, 110, and 112, respectively. Further, the following information of the refractive index of the materials must be assumed: the refractive index of air is 1.0, the refractive index of aqueous humor is approximately 1.33 and assuming both the first and second lenses 102, 108 are made from PMMA and the refractive index of PMMA is 1.49. The light at the outer surfaces, E and H, will be traveling from/to aqueous humor to/from PMMA, and the light at the inner surfaces, F and G, will be traveling from/to PMMA to/from air, respectively. Based on the above information, the effective power at each lens surface junction E, F, G and H are calculated and summed together to determine the total diopter power of the entire intraocular lens system.

When the ciliary body 24 relaxes, a negative potential 178 will occur which has a similar magnitude as the positive potential 176 that occurs when the ciliary body 24 contracts. As illustrated in FIG. 4b, when a negative potential 178 is generated within and around the ciliary body 24, the segment of positively charged fluid 146 is drawn toward the ciliary body 24 and the segment of negatively charged fluid 148 is repelled away from the ciliary body 24. The positively charged fluid segment 146 will begin to fill the fluid receptacle 180 as the pull of the negative potential draws the positive fluid towards the ciliary body 24 without allowing the positively charged fluid segment 146 to flow to the other side of the continuous flow loop 116. As the negatively charged fluid segment 148 moves away from the ciliary body 24 and the positively charge fluid segment 146 is drawn towards the ciliary body 24, the other fluid segments are forced to move through the continuous flow path 126. The fluid segments are positioned in the continuous flow loops 116 such that when the positively charged fluid segment 146 is drawn toward the ciliary body 24, the fluid segment containing water 152 is forced into the optical zone 118 of the lens. The segment of water 152 will substantially fill at least the fluid reservoir 114 between the first and second lenses 102, 108 and the fluid channel 120 in the first lens 102 within the optical zone 118 of the lens system.

As described above in connection with FIG. 2b, the effective diopter power of the lens system is the sum of the power at each lens surface junction. In the lens system illustrated in FIG. 4b, there are four surface junctions E, F, G and H. The effective power at each junction E, F, G and H can be calculated using equation 1 above, depending on the radius of curvature, in meters, of each corresponding lens surface 104, 106, 110 and 112, respectively. Further, the following information of the refractive index of the materials must be assumed: the refractive index of water is 1.33, the refractive index of aqueous humor is approximately 1.33 and assuming both the first and second lenses 102, 108 are made from PMMA and the refractive index of PMMA is 1.49. When the segment of water 152 is used to separate the first and second lenses 102, 108 made of PMMA, the light at the outer surfaces, E and H, will be traveling from/to aqueous humor to/from PMMA, and the light at the inner surfaces, F and G, will be traveling from/to PMMA to/from water, respectively. Based on the above information, the effective power at each lens surface junction E, F, G and H are calculated and summed together to determine the total diopter power of the entire intraocular lens system.

The effective diopter power of the lens configuration illustrated in FIG. 4b is a sum of power four surface junctions E, F, G and H, where all four surface junctions, E, F, G and H, have a very low power. The effective diopter power of the lens system in the configuration illustrated in FIG. 4a will have a higher power than the configuration illustrated in FIG. 4b, since two of the four surface junctions E, F, G, and H in FIG. 4a will have an increased power when air is positioned between the two lenses while all four surface junctions E, F, G, and H in FIG. 4b have a low power when water is positioned between the two lenses.

When the ciliary body 24 contracts to focus on a close image, the power of the intraocular lens system of the present invention will increase by preferably forcing a segment of air 150 into the optical zone 118 of the lens system. When the ciliary body 24 relaxes to focus on a far image, the power of the dual lens system will decrease by preferably forcing a segment of water 152 or a segment of another optically active fluid 154 into the optical zone 118 of the intraocular lens system. Although in the preferred embodiment, the segment of water 152 has been chosen to be forced into the optical zone 118 when the ciliary body 24 relaxes and the segment of air 150 has been chosen to be forced into the optical zone 118 when the ciliary body 24 contracts, other biocompatible fluids may be selected depending on the type of accommodation that is desired.

An alternate single lens embodiment 200 of the intraocular lens system of the present invention is illustrated in FIGS. 5a and 5b. The alternate embodiment 200 of the intraocular lens system comprises a single lens 202 with an internal fluid reservoir 204 formed in an optical zone 206 of the single lens 202. The fluid reservoir 204 has four fluid exit channels 208 which are preferably positioned with a first channel 210 in a 12 o'clock position, a second channel 212 at an 11 o'clock position, a third channel 214 at a 5 o'clock position and a fourth channel 216 at a 6 o'clock position, all positions are respective to the 12 o'clock position of the first channel 210. A pair of first 218 and second 220 continuous flow loops are attached to the exit channels 208 with the first and second flow loops 218, 220 each connecting two adjacent exit channels 208. Thus, a first flow loop 218 will connect the first 210 and second 212 exit channels and the second flow loop 220 will connect the third 214 and fourth 216 exit channels.

The single IOL lens 202 of the alternate embodiment 200 is preferably made of PMMA, but can be formed of any other suitable biocompatible lens material. The lens 202 is preferably between 4 mm and 7 mm in diameter and between 0.5–4 mm in thickness. The IOL lens 202 can be formed using conventional IOL molding techniques, however any other known lens forming techniques known to one skilled in the art can be used.

The internal fluid reservoir 204 of the single lens embodiment 200 is preferably a bio-concave circular cavity of approximately 3 mm to 5 mm in diameter. Preferably, the volume of fluid contained in the fluid reservoir 204 is proportional to the level of accommodation needed by the patient. The bio-concave surfaces of the fluid reservoir 204 form two lens surfaces within the lens resulting in a single lens embodiment with four individual lens surfaces. The internal fluid reservoir 204 is preferably formed during the molding process of the lens 202. However, the internal reservoir 204 can also be formed in the lens 202 by conventional boring techniques or other methods known to those skilled in the lens making art.

The exit channels 208 which are similar to the channels of the dual lens embodiment 100 can be formed during the molding step or by mechanical drilling, laser drilling, or by any other means which will be appreciated by one skilled in the art.

The first and second fluid flow loops 218, 220 are preferably formed of pieces of narrow transparent tubing as described in the previous embodiment and are connected to the exit channels 208 by the same boding means as described in connection with attaching the narrow tubing to the fluid path 126 of the previous embodiment 100.

Figure 6:
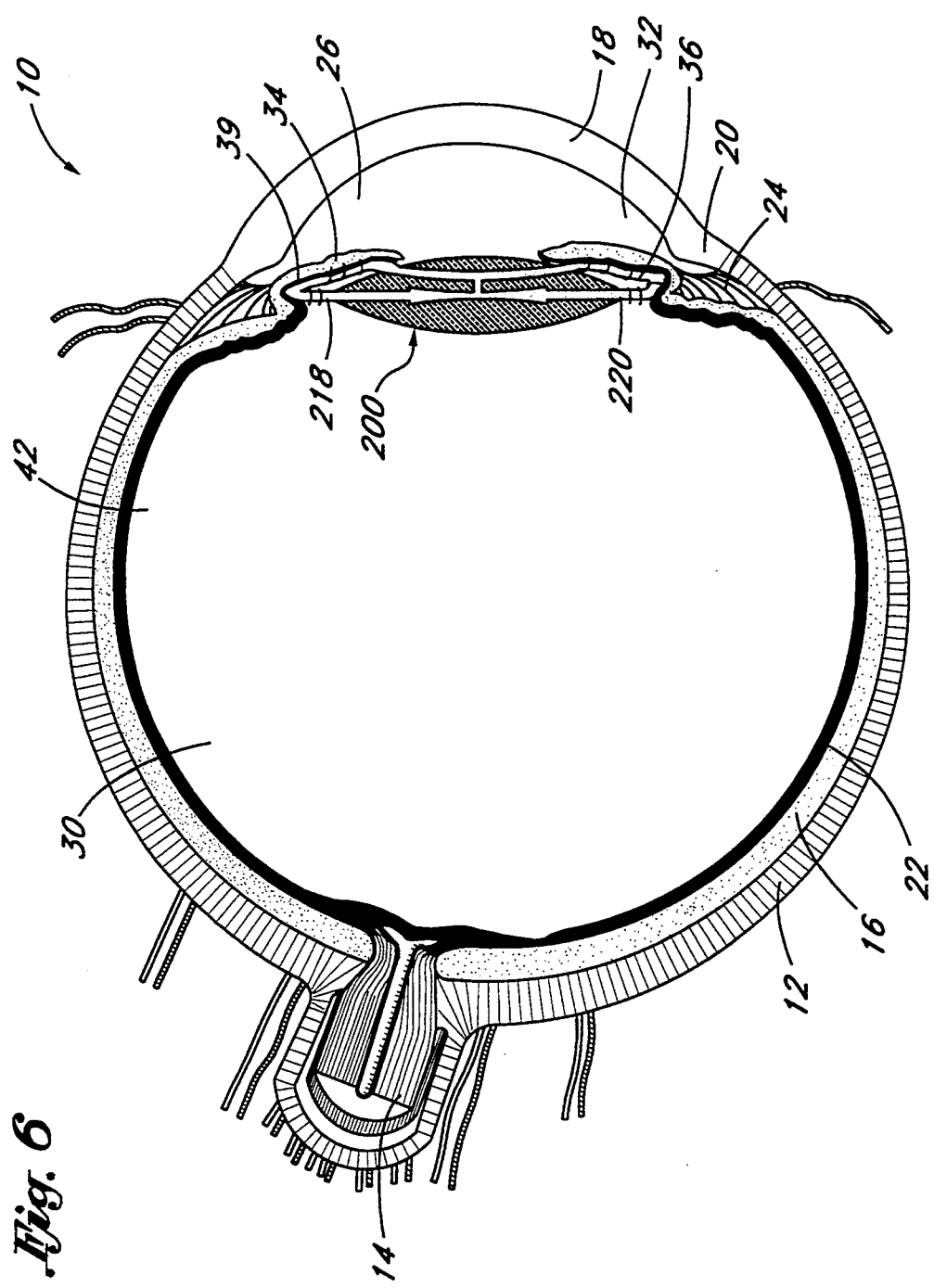
FIG. 6 is a cross sectional view of the alternative embodiment of the intraocular lens system illustrated in FIGS. 5a and 5b implanted in a human eye illustrating the position of the intraocular lens within the eye.

The operation of the alternate embodiment is similar to the previously described embodiment 100 illustrated in FIG. 3b, except that the fluid reservoir 204 is internal to the lens 202. As illustrated in the cross sectional diagram of FIG. 5b, there are also four lens surface junctions K, L, M, and N which correspond to the lens surface junctions F, G, H and J of FIG. 3b. The alternate embodiment 200 of the lens system of the present invention has a similar appearance to a conventional intraocular lens system with a single lens and two control haptics. This embodiment will enable the installation of the multi-focal lens system without requiring the conventional intraocular lens installation procedure to be substantially altered. In addition, the shape, size and feel of the single lens embodiment of the intraocular lens system of the present invention will be more familiar to the user's of IOLs and will make the system easier to insert in the patient's eye 10. FIG. 6 illustrates the alternate single lens embodiment 200 of the intraocular lens system of the present invention inserted within the eye of a patient. The lens lies in the posterior chamber 36 of the eye 10 with the haptics attached to the ciliary sulcus 39.

FIG. 7a is a cross sectional view of another alternate embodiment 300 of the intraocular lens system of the present invention which utilizes meniscus lenses in an eye focussing on a far object. The meniscus lens 300 of the intraocular lens system comprises a first meniscus lens 302, a second meniscus lens 304, an inner biconvex circular fluid reservoir 306, a thin transparent flexible membrane 308 stretched between the first lens 302 and second lens 304 which divides the fluid reservoir 306 into first 310 and second chambers 312. The first and second lenses 302, 304 are preferably made of PMMA, but can be formed of any other suitable biocompatible lens material. The first and second lenses 302, 304 can be formed using conventional IOL molding techniques, however any other known lens forming techniques known to one skilled in the art can be used.

The meniscus lens embodiment 300 is assembled by taking the second meniscus lens 304 and attaching the thin membrane 308 along the edge of the back portion of the lens 304 using a suitable biocompatible adhesive compound. The first meniscus lens 302 is then attached to the membrane 308 and to the second lens 304 along its edge using the biocompatible adhesive compound. The assembly process forms the fluid reservoir 306 between the first and second meniscus lenses 302, 304.

The fluid reservoir 306 has four fluid exit channels. Preferably, two exit channels are formed in the first meniscus lens 302 and two exit channels are formed in the second meniscus lens 304. The channels are preferably positioned with a first channel 316 in a 12 o'clock position, a second channel 318 at an 10 o'clock position, a third channel 320 at a 6 o'clock position and a fourth channel 322 at a 4 o'clock position, all positions are respective to the 12 o'clock position of the first channel 316. The exit channels can be formed during the molding of the first and second meniscus lenses 302, 302 or by mechanical drilling, laser drilling, or by any other means which will be appreciated by one skilled in the art.

A pair of first 324 and second 326 continuous flow loops are attached to the exit channels with the first and second flow loops 324, 326 each connecting two adjacent exit channels. As illustrated in FIG. 7a, the flow loops 324, 326 enable fluid communication between the first chamber 310 of the fluid reservoir and the second chamber 312 of the fluid reservoir 306. Thus, a first flow loop 324 will connect the first 316 and second 318 exit channels, and the second flow loop 326 will connect the third 320 and fourth 322 exit channels to enable communication between the first and second 310, 312 chambers of the fluid reservoir 306.

The first and second flow loops 324, 326 are preferably formed of pieces of narrow transparent tubing as described in the previous embodiment and are connected to the exit channels by the same boding means as described in connection with attaching the narrow tubing to the fluid path 126 of the previous embodiment 100. The first and second flow loops 324, 326 contain at least one segment of charged fluid 328 and at least one segment of optically active fluid 329. The fluid is introduced into the flow loops as discussed above. Preferably the first and second flow loops 324, 326 include the addition of two fluid receptacles 330. The fluid receptacles 330 are positioned in the continuous flow loops 324, 326 to trap a segment or segments of charged fluid 328, as discussed above, when the segments approach the ciliary body 24. Therefore, the addition of the fluid receptacles 330 to the flow loop 324, 326 will keep the segment(s) of charged fluid 328 on their respective sides of the flow loops 324, 326.

The internal fluid reservoir 306 of the meniscus lens embodiment 300 is preferably a bio-convex circular cavity of approximately 3 mm to 5 mm in diameter. Preferably, the volume of optically active fluid contained in the first 324 and second 324, 326 flow loops and the first segment 310 of the fluid reservoir 306 is proportional to the level of accommodation needed by the patient. The bio-convex surfaces of the fluid reservoir 306 form two lens surfaces within the lens resulting in a single lens embodiment with four individual lens surfaces. The thin flexible membrane 308 stretched across the center of the internal fluid reservoir 306 also acts as a lens surface. However, when the membrane is in its relaxed position surrounded by air on both sides, the effect on the power of the lens embodiment 300 is little, if any. When the membrane is stretched the effect on the power of the lens embodiment is increased.

The operation of the alternate embodiment 300 is similar to the previously described embodiment 100 illustrated in FIG. 3b, except that the flexible membrane 308 acts as an additional lens surface. As illustrated in the cross sectional diagram of FIGS. 7a-7b, there are five lens surface junctions O, P, Q, R and S; lens surfaces junctions O, P, R and S correspond to the lens surface junctions F, G, H and J of FIG. 3b while junction Q is caused by the addition of the thin flexible membrane 308. As illustrated in FIG. 7a when the ciliary body 24 is in the relaxed position, the first segment 310 of the inner fluid cavity 306 is filled with water and the second segment 312 is filled with air in equal proportions, therefore the flexible membrane 308 remains flat. The power of the lens surface Q is relatively small, compared to the other lens surfaces O, P, R and S. The flow loops 324, 326 are partially filled with an optically active fluid, such as water, and a segment or segments of charged fluid 328, such as a positively charged fluid which is used in this example. As discussed above, the overall power of the lens system in this state is the algebraic sum of the power at each individual lens surface, as calculated using equation 1 above. In this embodiment 300, the overall power of the lens system 300 is the sum of the power at surfaces O, P, Q, R, and S.

As illustrated in FIG. 7b, when the ciliary body fires, a charge 332 is produced, as described in connection with the first embodiment 100, we will consider the charge to be positive in this case. The segment of positively charged fluid 328 will be repelled by the positive potential created in and around the ciliary body 24. The movement of the positively charged fluid segment 326 away from the ciliary body 24 will force the optically active fluid to move around the flow loops 324, 326 and into the first segment 310 of the fluid reservoir 306. Simultaneously, the increase in pressure on the membrane 308 due to the addition of the optically active fluid 329 will force the air from the second segment 312 of the fluid reservoir 306 into the flow loops 324, 326. When an optically active fluid, such as water, is introduced into the first segment 310 of the inner chamber 306, the weight of the fluid may weigh on the thin flexible membrane 308 and stretch the membrane 308 which will change the radius of curvature of the membrane 308. Thus, the variation in the radius of curvature of the membrane 308 will alter the power of the lens surface Q in accordance with equation 1 above. As discussed above, the overall power of the lens system is the algebraic sum of the power at each individual lens surface, i.e., surfaces O, P, Q, R, and S in this case. Since, the only variation that occurred in the system was the altering of the radius of curvature of surface Q, the variation in the power of the entire lens system will be due to the variation in the radius of curvature of the membrane 308.

As the ciliary body 24 attempts to focus on a close object, the positive charge 324 disappears, and an opposite potential, i.e. a negative potential in this case, occurs in and around the ciliary body 24. When the opposite potential occurs, the positively charged fluid segment 328 will be drawn towards the ciliary body 24. As the positively charged fluid segment 328 moves, the optically active fluid will move from the first segment 310 back into the flow loops 324, 326 and will release the pressure on the membrane 308. As the optically active fluid returns to the flow loops 324, 326, the movement of the fluids in the flow loops 324, 326 will force the air back into the second chamber 312 of the inner cavity 306. Once the pressure from the movement of the fluids equalize, the membrane 308 will lie flat in the fluid reservoir 306, the lens system of the meniscus lens embodiment 300 will return to the configuration illustrated in FIG. 7a.

The alternate embodiment 300 of the lens system of the present invention has a similar appearance to a conventional intraocular lens system with a single lens look and two control haptics. This embodiment will enable the installation of the multi-focal lens system without requiring the conventional intraocular lens installation procedure to be substantially altered. In addition, the shape, size and feel of the meniscus lens embodiment 300 of the intraocular lens system of the present invention will be more familiar to the user's of IOLs and will make the system easier to insert in the patient's eye 10.

By using the electric potential that is generated when the ciliary body 24 relaxes and contracts to control the accommodation of the IOL system, a reliable system results. Other variable focus systems rely on an external energy source or external force to change the accommodation of the intraocular lens. By relying on an external signal or force to control the intraocular lens, there is a greater chance of misdetecting the external signal or reacting incorrectly. The system of the present invention is advantages as it relies on the natural signals that the eye 10 generates to control the accommodation of the crystalline lens 28 to control the accommodation of the artificial lens system of the present invention. Thus, the chances that the system of the present invention will misfocus are greatly reduced by relying only on signals generated by the eye 10. Further, the reliability and life cycle of an external power sources is not as high as the reliability and life cycle of the functions of the human body.

In addition, the present invention utilizes the potential energy from within and around the ciliary body generated during contraction and relaxation and transfers this electric potential into pressure energy. This pressure energy is used to mobilize fluid in and out of the lens system of the present invention. Although the voltage generated within the ciliary body is in the microvolt range, it is sufficient to mobilize the minute amount of fluid volume (within the nanoliter to microliter range) necessary to fill the internal cavity of the intraocular lens system.

Further, the system of the present invention can be modified to have more than two levels of accommodation. The fluid path 126 of the intraocular lens system can include a multitude of charged fluids some of greater charge strength than others, such that some fluids will only be attracted to the ciliary body 24 when the charge is above a certain magnitude and of a particular polarity. When the ciliary body 24 relaxes, a negative potential 178 occurs which has an equal magnitude as the positive potential 176 that occurs when the ciliary body 24 contracts. After the appearance of the negative potential 178 that occurs when the ciliary body 24 relaxes, a positive potential 176 will again occur with a lesser magnitude than the initial contraction, which is later followed by a negative potential 178 which is of a lesser magnitude than the initial potential. Different fluid segments which are attracted to the appearance of the potential energy at these lesser magnitudes can be arranged in the continuous flow path, thereby enabling the lens system of the present invention to provide a step function of variable accommodation depending on the polarity and magnitude of the potential generated around the ciliary body 24.

Lastly, the charged segments of fluid may vary in length, thus varying the volume or mass of charge, depending on the variation of muscle mass, i.e. power or electric potential which is created in and around the ciliary body 24, which is based on the variation of the electric potential that is generated in different patients. A single charged fluid segment may also be sufficient, as illustrated in the meniscus lens embodiment 300, to move the optically active fluid through the intraocular lens system of the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed:

1. A variable focus intraocular lens comprising:
   a first lens portion with at least one lens surface and at least one fluid channel;
   a second lens portion with at least one lens surface;
   an optical zone defined in the center of each of said first and second lens portions;
   a fluid reservoir between said first and second lens portions;
   at least one flow loop connecting said fluid reservoir to said fluid channel to define a fluid path, such that said fluid path contains multiple discrete segments of fluid which move through the fluid path, said multiple segments including at least one segment of charged solution.

2. The lens system defined in claim 1 wherein said discrete fluid segments further comprise at least one segment of positively charged solution, at least one segment of negatively charged solution, at least one segment of air, and at least two segments from the group consisting of oil, water and another biocompatible fluid.

3. The lens system defined in claim 2 wherein said discrete fluid segments move through said fluid path in response to the application of a positive potential.

4. The lens system defined in claim 3, wherein said segment of air is positioned in said optical zone in response to the application of said positive potential.

5. The lens system defined in claim 2 wherein said discrete fluid segments move through said fluid path in response to the application of a negative potential.

6. The lens system defined in claim 4, wherein one of said segments of oil, water or another fluid is positioned in said optical zone in response to the application of said negative potential.

7. A method of varying the accommodation of an intraocular lens system within an eye, utilizing the potential produced by the contraction and relaxation of a ciliary body of said eye comprising the steps of:
   increasing a diopter power of said intraocular lens system in response to an application of a positive potential produced by said ciliary body when said ciliary body contracts to said intraocular lens system; and
   decreasing the diopter power of said intraocular lens system in response to an application of a negative potential produced by said ciliary body when said ciliary body relaxes to said intraocular lens system.

8. An intraocular lens for implantation into an eye, comprising:
   a first lens surface;
   a second surface spaced apart from the first lens surface;
   a reservoir in between the first lens surface and the second surface;
   at least one flow path into and out of the reservoir;
   at least one segment of optical media movably disposed in the at least one flow path; and
   at least one segment of charged species movably disposed in the at least one flow path.

9. An intraocular lens as in claim 8, wherein the flow path provides a continuous flow loop through at least a portion of the reservoir.

10. An intraocular lens as in claim 9, further comprising a second continuous flow loop.

11. An intraocular lens as in claim 9, wherein said charged species comprises at least one segment of positively charged media movably disposed within the loop, and spaced apart from at least one segment of negatively charged media movably disposed within the loop.

12. An intraocular lens as in claim 11, wherein said positively charged media comprises a fluid having a cation therein.

13. An intraocular lens as in claim 8, wherein at least a portion of the reservoir lies within the optical zone of the lens.

14. An intraocular lens as in claim 8, wherein said lens is a double convex lens.

15. An intraocular lens as in claim 14, wherein said double convex lens further comprises a fluid flow path extending therethrough, for providing communication between the flow loop and the portion of the reservoir within the optical zone.

16. An intraocular lens system having variable optical properties, comprising:
   a first lens having a flow path extending therethrough;
   a second lens spaced apart from the first lens to define a reservoir therebetween;
   a first flow loop for providing fluid communication between a first end of the flow path and the reservoir;
   a second flow loop for providing fluid communication between a second end of the flow path and the reservoir;
   a branch flow path for providing fluid communication between the flow path in the first lens and the reservoir; and
   a fluid media disposed within at least a portion the flow path;
   wherein the fluid media is movable from a first position within the reservoir and a second position outside of the reservoir.

17. A flow system sized and configured for placement in the eye, said system for moving an optical media into and out of a reservoir in an intraocular lens, said system comprising:
   a flow path adapted to be positioned adjacent a muscle, the flow path being in fluid communication with the reservoir;
   at least one segment of charged media movably disposed within the flow path;
   a first optical media within the flow path, having a first refractive index; and
   at least one second optical media in the flow path having a second refractive index;
   wherein the first and the at least one second optical media are moved relative to the reservoir in response to an electrical potential generated by the muscle.

* * * * *